(12) United States Patent
Lorimer et al.

(10) Patent No.: US 8,466,173 B2
(45) Date of Patent: Jun. 18, 2013

(54) CRYSTAL FORMS OF (3R)-1-(2-METHYL-ALANYL-D-TRYPTOPHYL)-3-(PHENYL-METHYL)-3-PIPERIDINECARBOXYLIC ACID 1,2,2-TRIMETHYLHYDRAZIDE

(75) Inventors: Keith Lorimer, West Lafayette, IN (US); Seemon H. Pines, New Providence, NJ (US); Paul Bernhard, Slingerlands, NY (US); Benjamin Littler, San Diego, CA (US)

(73) Assignee: Helsinn Therapeutics (U.S.), Inc., Bridgewater, NJ (US)

( * ) Notice: Subject to any disclaimer, the term of this patent is extended or adjusted under 35 U.S.C. 154(b) by 224 days.

(21) Appl. No.: 12/831,009

(22) Filed: Jul. 6, 2010

(65) Prior Publication Data

US 2011/0003996 A1 Jan. 6, 2011

Related U.S. Application Data (63) Continuation of application No. 11/165,598, filed on Jun. 22, 2005, now Pat. No. 7,825,138.

(60) Provisional application No. 60/583,757, filed on Jun. 29, 2004.

(51) Int. Cl.
  *A61K 31/445* (2006.01)
  *C07D 401/06* (2006.01)

(52) U.S. Cl.
  USPC .......................... 514/323; 546/201

(58) Field of Classification Search
  USPC .......................... 514/323; 546/201
  See application file for complete search history.

(56) References Cited

U.S. PATENT DOCUMENTS

| | | |
|---|---|---|
| 6,303,620 B1 | 10/2001 | Hansen et al. |
| 6,576,648 B2 | 6/2003 | Ankersen |
| 7,825,138 B2 | 11/2010 | Lorimer et al. |
| 2001/0041720 A1 | 11/2001 | Ankersen |

OTHER PUBLICATIONS

Dean "Analyticl Chem . . . " p. 10.24-10.26 (1993).*
Bernstein "Polymorphism in molecular crystals" p. 115-118, 272 (2002).*
Braga et Al. "Making crystals . . . " J. Roy. Soc, Chem. Chem. Commun. p. 3635-3645 (2005).*
Polymorphism "Scientific consideration . . . " ACPS meeting p. 1-5 (2002).*
Seddon "Pseudopolymorph . . . " Cryst. grow design v. 4(6) p. 1047 (2004).*
Vippagunta et al. "Crystalline solids" Adv. Drug. Del. Rev. 48, p. 3-26 (2001).*
Seddon "Pseudomorph . . . " Crystal growth and design v.4(6) p. 1087 (2004) (p. 1-2 internet print).
Bennett "chemical dictionary" p. 553 (1976).
Niazi "handbook of . . . " (2009) (one page from internet).
Seddon "Pseudopolymorph . . . " Crystal growth & design v.4(6) p. 1087 (2004) (2 page from internet).
Kirk-Othmer "Encyclopedia of chemical technology" p. 95-147 (2002).
Cheronis "Semimicro experimental organic chemistry" p. 31-43 (1958).
Fujiwara et al. "First principales and direct design . . . " J. Process control v. 15, p. 493-504 (2005).
Borchardt et al. "Pharmaceutical profiling . . . " p. 93-125 (2004).
International Search Report, PCT/US2005/022408, Nov. 2, 2005.
Chyall, Leonard J., Ph.D., "Current Applications of X-Ray Powder Diffraction in the Pharmaceutical Industry," American Pharmaceutical Review, Oct. 3, 2012, http://www.americanpharmaceuticalreview.com/Featured-Articles/122323-Current-Applications-of-X-Ray-Powder-Diffraction-in-the-Pharmaceutical-Industry/.
Suzuki, Tetsuya, et al., "Characterization of Non-stoichiometric Hydration and the Dehydration Behavior of Sitafloxacin Hydrate," Chem. Pharm. Bull. 60(1), pp. 45-55, 2012.

* cited by examiner

*Primary Examiner* — Celia Chang
(74) *Attorney, Agent, or Firm* — Arnall Golden Gregory LLP; Clark G. Sullivan (57) ABSTRACT

Crystalline polymorphs of (3R)-1-(2-methylalanyl-D-tryptophyl)-3-(phenylmethyl)-3-piperidinecarboxylic acid 1,2,2-trimethylhydrazide which are useful as pharmaceutical agents are disclosed. Methods of production and isolation of these polymorphs and pharmaceutical compositions which include these polymorphs and pharmaceutical methods of treatment are also disclosed. The crystalline polymorphs of the present invention are useful as they act directly on the pituitary gland cells to release growth hormone.

17 Claims, 5 Drawing Sheets

CRYSTAL FORMS OF (3R)-1-(2-METHYL-ALANYL-D-TRYPTOPHYL)-3-(PHENYL-METHYL)-3-PIPERIDINECARBOXYLIC ACID 1,2,2-TRIMETHYLHYDRAZIDE

CROSS REFERENCE TO RELATED APPLICATIONS

This application is a continuation of U.S. application Ser. No. 11/165,598, filed Jun. 22, 2005 now U.S. Pat. No. 7,825,138, which claims the benefit of U.S. Provisional Application No. 60/583,757, filed on Jun. 29, 2004. Each of the above-named applications is hereby incorporated by reference in its entirety.

BACKGROUND OF THE INVENTION

Growth hormone is a major participant in the control of several complex physiologic processes, including growth and metabolism. Growth hormone is known to have a number of effects on metabolic processes, e.g., stimulation of protein synthesis and free fatty acid mobilization and to cause a switch in energy metabolism from carbohydrate to fatty acid metabolism. Deficiency in growth hormone can result in a number of severe medical disorders, e.g., dwarfism.

The release of growth hormone from the pituitary is controlled, directly or indirectly, by number of hormones and neurotransmitters. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example, arginine, L-3,4-dihydroxyphenylalanine (1-Dopa), glucagon, vasopressin, PACAP (pituitary adenylyl cyclase activating peptide), muscarinic receptor agonists and a synthetic hexapeptide, GHRP (growth hormone releasing peptide) release endogenous growth hormone either by a direct effect on the pituitary or by affecting the release of GHRH and/or somatostatin from the hypothalamus.

The use of certain compounds for increasing the levels of growth hormone in mammals has previously been proposed. For example, U.S. Pat. Nos. 6,303,620 and 6,576,648 (the entire contents of which are incorporated herein by reference), disclose a compound: (3R)-1-(2-methylalanyl-D-tryptophyl)-3-(phenylmethyl)-3-piperidinecarboxylic acid 1,2,2-trimethylhydrazide, having the following chemical structure:

which acts directly on the pituitary cells under normal experimental conditions in vitro to release growth hormone therefrom. This growth hormone releasing compound can be utilized in vitro as a unique research tool for understanding, inter alia, how growth hormone secretion is regulated at the pituitary level. Moreover, this growth hormone releasing compound can also be administered in vivo to a mammal to increase endogenous growth hormone release.

SUMMARY OF THE INVENTION

It has been found that (3R)-1-(2-methylalanyl-D-tryptophyl)-3-(phenylmethyl)-3-piperidinecarboxylic acid 1,2,2-trimethylhydrazide can be crystallized. At least four crystalline forms with purities of greater than 99 area percent have been produced. These crystalline forms of (3R)-1-(2-methylalanyl-D-tryptophyl)-3-(phenylmethyl)-3-piperidinecarboxylic acid 1,2,2-trimethylhydrazide are expected to be useful as pharmaceutical compositions, which can be used to increase endogenous growth hormone release.

In one embodiment, the present invention is crystalline (3R)-1-(2-methylalanyl-D-tryptophyl)-3-(phenylmethyl)-3-piperidinecarboxylic acid 1,2,2-trimethylhydrazide.

In another embodiment, the present invention is crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one or at least two 2θ values measured using Cu $K_\alpha$ radiation are selected from the group consisting of about: 10.1, 11.1, 17.6, 20.0 and 20.8. In yet another embodiment, the present invention is a crystalline composition, having an X-ray powder diffraction pattern wherein at least one or at least two 2θ values measured using Cu $K_\alpha$ radiation are selected from the group listed above and at least one or at least two 2θ values measured using Cu $K_\alpha$ radiation are selected from the group consisting of about: 9.6, 17.3, 18.2, 22.1 and 23.5.

In another embodiment, the present invention is crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one or at least two 2θ values measured using Cu $K_\alpha$ radiation are selected from the group consisting of about: 17.0, 19.4, 21.5, 26.2, and 33.3. In yet another embodiment, the present invention is a crystalline composition, having an X-ray powder diffraction pattern wherein at least one or at least two 2θ values measured using Cu $K_\alpha$ radiation are selected from the group listed above and at least one or at least two 2θ values measured using Cu $K_\alpha$ radiation are selected from the group consisting about: 9.3, 23.3, 20.4, 22.9, and 23.5.

In another embodiment, the present invention is crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one or at least two 2θ values measured using Cu $K_\alpha$ radiation are selected from the group consisting of about 19.2, 20.1, 23.0, 26.2, and 27.0. In yet another embodiment, the present invention is a crystalline composition, having an X-ray powder diffraction pattern wherein at least one or at least two 2θ values measured using Cu $K_\alpha$ radiation are selected from the group listed above and at least one or at least two 2θ values measured using Cu $K_\alpha$ radiation are selected from the group consisting about: 16.3, 21.4, 24.0, 29.8, and 31.5.

In another embodiment, the present invention is crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one or at least two 2θ values measured using Cu $K_\alpha$ radiation are selected from the group consisting of about 10.2, 11.2, 18.7, 20.6, and 23.4. In yet another embodiment, the present invention is a crystalline composition, having an X-ray powder diffraction pattern wherein at least one or at least two 2θ values measured using Cu $K_\alpha$ radiation are selected from the group listed above and at least one or at least two 2θ values measured using Cu $K_\alpha$ radiation are selected from the group consisting of about 9.9, 13.8, 14.3, 16.7, and 19.8.

In another embodiment, the present invention is crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one 2θ value measured using Cu $K_\alpha$ radiation is selected from the group consisting of: 10.1, 17.0, 20.6, and 23.0, and optionally a second additional 2θ value measured using Cu $K_\alpha$ radiation is selected from the group consisting of about: 17.6, 19.2, 23.0, 23.4, 26.2, and 33.3 or optionally a second additional 2θ value measured using Cu $K_\alpha$ radiation is selected from the group consisting of: 9.5, 16.7, 17.5, 17.9, 20.0, 21.5, 23.5, 23.9, and 27.5.

Further the present invention is directed to a process for preparing crystalline (3R)-1-(2-methylalanyl-D-tryptophyl)-3-(phenylmethyl)-3-piperidinecarboxylic acid 1,2,2-trimethylhydrazide. The method comprises combining (3R)-1-(2-methylalanyl-D-tryptophyl)-3-(phenylmethyl)-3-piperidinecarboxylic acid 1,2,2-trimethylhydrazide with a solvent. Precipitating the crystals from the solvent and isolating the crystals. In one embodiment, the solvent is selected from the group consisting of: water, methanol, ethanol, n-propanol, isopropanol, butanol, and mixtures thereof. In another embodiment, the solvent is a mixture of methanol and water. In a further embodiment, the solvent includes between 40% v/v methanol and 60% v/v methanol. In a still further embodiment, the present invention is crystalline (3R)-1-(2-methylalanyl-D-tryptophyl)-3-(phenylmethyl)-3-piperidinecarboxylic acid 1,2,2-trimethylhydrazide produced by the method described above.

Further the present invention is a process for preparing crystalline (3R)-1-(2-methylalanyl-D-tryptophyl)-3-(phenylmethyl)-3-piperidinecarboxylic acid 1,2,2-trimethylhydrazide. The method comprises the steps of combining {1-[(1R)-2-](3R)-3-Benzyl-3-(N,N',N'-trimethylhydrazinocarbonyl)piperidin-1-yl-]-1-(1H-indol-3-ylmethyl)-2-oxo-ethylcarbamoyl]-1-methylethyl}carbamic acid tert-butyl ester with a solvent and an acid. The method further comprises neutralizing the mixture, precipitating the crystals from the solvent, and isolating the crystals. In one embodiment the solvent is methanol, and the mixture is neutralized with a mixture of potassium hydroxide and water. In another embodiment the acid is methanesulfonic acid. In yet another embodiment the present invention is a crystalline (3R)-1-(2-methylalanyl-D-tryptophyl)-3-(phenylmethyl)-3-piperidinecarboxylic acid 1,2,2-trimethylhydrazide produced by the method described above.

Further, the present invention is directed to a pharmaceutical composition comprising crystalline (3R)-1-(2-methylalanyl-D-tryptophyl)-3-(phenylmethyl)-3-piperidinecarboxylic acid 1,2,2-trimethylhydrazide and at least one pharmaceutically acceptable carrier or diluent.

Further the present invention is directed to a method of stimulating the release of growth hormone from the pituitary of a mammal, the method comprising administering to said mammal a therapeutically effective amount of crystalline (3R)-1-(2-methylalanyl-D-tryptophyl)-3-(phenylmethyl)-3-piperidinecarboxylic acid 1,2,2-trimethylhydrazide.

The present invention provides crystalline polymorphic forms of (3R)-1-(2-methylalanyl-D-tryptophyl)-3-(phenylmethyl)-3-piperidinecarboxylic acid 1,2,2-trimethylhydrazide, each of which are more stable, and have advantageous manufacturing properties relative to amorphous forms of this compound. Due to the high purity of these crystalline forms, they can fulfill more exacting pharmaceutical regulations and specifications often required for pharmaceutical formulations. Furthermore, the polymorphs of the present invention are readily suspended in solvents, they are easily dried and filtered, and as such are amenable to large-scale production. Additionally, these crystalline forms are stable for extended periods of time without the need for specialized storage conditions.

DETAILED DESCRIPTION OF THE INVENTION

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The present invention is directed to crystalline compounds of the following Structural Formula:

The chemical name of Formula I is 1-(2-methylalanyl-D-tryptophyl)-3-(phenylmethyl)-3-piperidinecarboxylic acid 1,2,2-trimethylhydrazide which is the equivalent of 2-amino- N-[(1R)-2-[-3-benzyl-3-(N,N',N'-trimethylhydrazinocarbo-nyl)piperi-din-1-yl]-1-((1H-indol-3-yl)methyl)-2-oxoethyl]-2-methylpropionamide.

In a preferred embodiment, the compound of Formula I has the (R) configuration at the chiral carbon designated by the asterisk (*) in Formula I. The chemical name of the compound of Formula I having the (R) configuration at the designated chiral carbon is: (3R)-1-(2-methylalanyl-D-tryptophyl)-3-(phenylmethyl)-3-piperidinecarboxylic acid 1,2,2-trimethylhydrazide:

II

It is to be understood that crystalline (3R)-1-(2-methylalanyl-D-tryptophyl)-3-(phenylmethyl)-3-piperidinecarboxylic acid 1,2,2-trimethylhydrazide includes hydrates thereof, unless specifically excluded. In a preferred embodiment crystalline (3R)-1-(2-methylalanyl-D-tryptophyl)-3-(phenylmethyl)-3-piperidinecarboxylic acid 1,2,2-trimethylhydrazide is in the form of a dihydrate. As used herein a "dihydrate" is when each molecule of (3R)-1-(2-methylalanyl-D-tryptophyl)-3-(phenylmethyl)-3-piperidinecarboxylic acid 1,2,2-trimethylhydrazide is associated with about two molecules of water. As used herein a "monohydrate" is when each molecule of (3R)-1-(2-methylalanyl-D-tryptophyl)-3-(phenylmethyl)-3-piperidinecarboxylic acid 1,2,2-trimethylhydrazide is associated with about one molecule of water.

As used herein a "crystalline form" is a solid substance having a highly regular chemical structure. When a compound recrystallizes from a solution or slurry, it may crystallize with different spatial lattice arrangements, a property referred to as "polymorphism," with the different crystal forms individually being referred to as a "polymorph." While polymorphs of a given substance have the same chemical composition, they may differ from each other with respect to one or more physical properties, such as solubility and dissociation, true density, melting point, crystal shape, compaction behavior, flow properties, and/or solid state stability.

The polymorphic behavior of drugs can be of crucial importance in pharmacy and pharmacology. The differences in physical properties exhibited by polymorphs affect pharmaceutical parameters such as storage stability, compressibility and density (important in formulation and product manufacturing), and dissolution rates (an important factor in determining bio-availability). Differences in stability can result from changes in chemical reactivity (e.g. differential oxidation, such that a dosage form discolors more rapidly when it is one polymorph than when it is another polymorph) or mechanical changes (e.g. tablets crumble on storage as a kinetically favored polymorph converts to thermodynamically more stable polymorph) or both (e.g. tablets of one polymorph are more susceptible to breakdown at high humidity). In addition, the physical properties of the crystal may be important in processing: for example, one polymorph might be more likely to form solvates or might be difficult to filter and wash free of impurities (i.e. particle shape and size distribution might be different between one polymorph relative to other).

In certain specific embodiments, the present invention is directed to crystalline polymorphs of (3R)-1-(2-methylalanyl-D-tryptophyl)-3-(phenylmethyl)-3-piperidinecarboxylic acid 1,2,2-trimethylhydrazide. Four such crystalline polymorphs described herein are designated as crystalline forms A, B, C, and D, and may be distinguished by their respective X-ray powder diffraction patterns. Crystalline forms A, B, C, and D of the present invention may exist in anhydrous forms as well as hydrated and solvated forms, all of which are intended to be encompassed within the scope of the present invention.

In one embodiment, X-ray powder diffraction patterns of the polymorphs are measured on a Shimadzu XRD-6000 X-ray powder diffractometer using Cu $K_\alpha$ radiation. The instrument is equipped with a fine focus X-ray tube. The tube voltage and amperage ware set to 40 kV and 40 mA, respectively. The divergence and scattering slits are set at 1° and the receiving slit is set at 0.15 mm. Diffracted radiation is detected by NaI scintillation detector. A theta-two theta continuous scan at 3°/min (0.4 sec/0.02° step) from 2.5 to 40° 2θ is used. A silicon standard is analyzed to check the instrument alignment. Samples were prepared for analysis by placing them in an aluminium holder with silicon insert. Some shifting in peak positions can occur due to differences in sample height. As defined herein, the 2-theta position has an error of +/−0.2°. Further, some shifting in peak positions can occur due to differences in the sample, such as, for example, particle size and crystal density.

In one specific embodiment, the present invention is directed to crystalline form A of (3R)-1-(2-methylalanyl-D-tryptophyl)-3-(phenylmethyl)-3-piperidinecarboxylic acid 1,2,2-trimethylhydrazide, produced by slow evaporation from a solution thereof as described in Example 1, characterized by the following X-ray powder diffraction pattern (also presented in FIG. 1) expressed in terms of 2θ, d-spacings and relative intensities:

TABLE 1

Peak Data List for crystalline form A of (3R)-1-(2-methylalanyl-D-tryptophyl)-3-(phenylmethyl)-3-piperidinecarboxylic acid 1,2,2-trimethylhydrazide

| Peak No. | 2Theta (deg) | d (A) | Relative Intensity |
|---|---|---|---|
| 1 | 2.6 | 33.7 | 3 |
| 2 | 2.9 | 30.6 | 4 |
| 3 | 4.0 | 22.34 | 3 |
| 4 | 4.7 | 18.8 | 3 |
| 5 | 7.1 | 12.4 | 3 |
| 6 | 9.3 | 9.5 | 8 |
| 7 | 16.1 | 5.5 | 4 |
| 8 | 16.6 | 5.3 | 4 |
| 9 | 17.0 | 5.2 | 100 |
| 10 | 17.6 | 5.0 | 6 |
| 11 | 19.4 | 4.6 | 9 |
| 12 | 20.1 | 4.4 | 3 |
| 13 | 20.4 | 4.4 | 8 |
| 14 | 20.6 | 4.3 | 4 |
| 15 | 21.5 | 4.1 | 10 |
| 16 | 22.9 | 3.9 | 7 |
| 17 | 23.1 | 3.9 | 6 |
| 18 | 23.3 | 3.8 | 6 |
| 19 | 23.5 | 3.8 | 9 |
| 20 | 24.1 | 3.7 | 4 |

TABLE 1-continued

Peak Data List for crystalline form A of (3R)-1-(2-methylalanyl-
D-tryptophyl)-3-(phenylmethyl)-3-piperidinecarboxylic acid
1,2,2-trimethylhydrazide

| Peak No. | 2Theta (deg) | d (A) | Relative Intensity |
|---|---|---|---|
| 21 | 25.4 | 3.5 | 4 |
| 22 | 26.2 | 3.4 | 37 |
| 23 | 26.5 | 3.4 | 4 |
| 24 | 27.1 | 3.3 | 6 |
| 25 | 27.4 | 3.3 | 5 |
| 26 | 29.8 | 3.0 | 6 |
| 27 | 30.0 | 3.0 | 4 |
| 28 | 30.7 | 2.9 | 4 |
| 29 | 30.9 | 2.9 | 3 |
| 30 | 31.5 | 2.8 | 5 |
| 31 | 33.3 | 2.7 | 18 |
| 32 | 34.7 | 2.6 | 4 |
| 33 | 35.1 | 2.6 | 3 |
| 34 | 37.2 | 2.4 | 4 |
| 35 | 37.3 | 2.4 | 5 |
| 36 | 37.5 | 2.4 | 4 |
| 37 | 37.9 | 2.4 | 3 |
| 38 | 38.1 | 2.4 | 3 |
| 39 | 38.4 | 2.3 | 4 |
| 40 | 38.8 | 2.3 | 4 |

In another embodiment, the present invention is directed to crystalline form B of (3R)-1-(2-methylalanyl-D-tryptophyl)-3-(phenylmethyl)-3-piperidinecarboxylic acid 1,2,2-trimethylhydrazide, produced by slow evaporation from a solution thereof as described in Example 2, characterized by the following X-ray powder diffraction pattern (also presented in FIG. 2) expressed in terms of 2θ, d-spacings and relative intensities:

TABLE 2

Peak Data List for crystalline form B of (3R)-1-(2-methylalanyl-
D-tryptophyl)-3-(phenylmethyl)-3-piperidinecarboxylic acid
1,2,2-trimethylhydrazide

| Peak No. | 2Theta (deg) | D (A) | Relative Intensity |
|---|---|---|---|
| 1 | 8.1 | 10.9 | 8 |
| 2 | 9.0 | 9.8 | 4 |
| 3 | 9.6 | 9.2 | 8 |
| 4 | 10.7 | 8.3 | 4 |
| 5 | 13.6 | 6.5 | 8 |
| 6 | 14.3 | 6.2 | 12 |
| 7 | 16.3 | 5.4 | 40 |
| 8 | 17.5 | 5.1 | 12 |
| 9 | 18.0 | 4.9 | 12 |
| 10 | 19.2 | 4.6 | 68 |
| 11 | 20.1 | 4.4 | 56 |
| 12 | 21.4 | 4.2 | 20 |
| 13 | 23.0 | 3.9 | 100 |
| 14 | 24.0 | 3.7 | 16 |
| 15 | 24.6 | 3.6 | 4 |
| 16 | 25.3 | 3.5 | 12 |
| 17 | 26.2 | 3.4 | 100 |
| 18 | 27.0 | 3.3 | 52 |
| 19 | 29.8 | 3.0 | 16 |
| 20 | 31.5 | 2.8 | 32 |
| 21 | 33.1 | 2.7 | 16 |
| 22 | 34.1 | 2.6 | 12 |
| 23 | 35.3 | 2.5 | 8 |
| 24 | 37.4 | 2.4 | 4 |
| 25 | 38.6 | 2.3 | 8 |

In another embodiment, the present invention is directed to crystalline form C of (3R)-1-(2-methylalanyl-D-tryptophyl)-3-(phenylmethyl)-3-piperidinecarboxylic acid 1,2,2-trimethylhydrazide, produced by slow evaporation from a solution thereof as described in Example 3.

In another embodiment, the present invention is directed to crystalline form D of (3R)-1-(2-methylalanyl-D-tryptophyl)-3-(phenylmethyl)-3-piperidinecarboxylic acid 1,2,2-trimethylhydrazide, produced by slow evaporation from a solution thereof as described in Example 5, characterized by the following X-ray powder diffraction pattern (also presented in FIG. 3) expressed in terms of 2θ, d-spacings and relative intensities:

TABLE 3

Peak Data List for crystalline form D of (3R)-1-(2-methylalanyl-
D-tryptophyl)-3-(phenylmethyl)-3-piperidinecarboxylic acid
1,2,2-trimethylhydrazide

| Peak No. | 2Theta (deg) | d (A) | Relative Intensity |
|---|---|---|---|
| 1 | 9.4 | 9.4 | 3 |
| 2 | 9.9 | 9.0 | 24 |
| 3 | 10.2 | 8.7 | 76 |
| 4 | 10.6 | 8.3 | 15 |
| 5 | 11.2 | 7.9 | 55 |
| 6 | 11.7 | 7.6 | 8 |
| 7 | 13.8 | 6.4 | 24 |
| 8 | 14.3 | 6.2 | 43 |
| 9 | 14.6 | 6.1 | 9 |
| 10 | 15.1 | 5.9 | 24 |
| 11 | 16.7 | 5.3 | 24 |
| 12 | 17.4 | 5.1 | 18 |
| 13 | 17.9 | 5.0 | 23 |
| 14 | 18.2 | 4.9 | 15 |
| 15 | 18.7 | 4.7 | 53 |
| 16 | 19.8 | 4.5 | 40 |
| 17 | 20.6 | 4.3 | 100 |
| 18 | 21.1 | 4.2 | 5 |
| 19 | 21.6 | 4.1 | 9 |
| 20 | 21.8 | 4.1 | 10 |
| 21 | 22.5 | 4.0 | 7 |
| 22 | 23.4 | 3.8 | 56 |
| 23 | 23.8 | 3.7 | 6 |
| 24 | 24.9 | 3.6 | 9 |
| 25 | 25.8 | 3.5 | 13 |
| 26 | 26.4 | 3.4 | 6 |
| 27 | 27.5 | 3.2 | 11 |
| 28 | 27.7 | 3.2 | 21 |
| 29 | 28.8 | 3.1 | 13 |
| 30 | 30.0 | 3.0 | 14 |
| 31 | 30.4 | 3.0 | 18 |
| 32 | 31.3 | 2.9 | 13 |
| 33 | 31.9 | 2.8 | 6 |
| 34 | 32.9 | 2.7 | 4 |
| 35 | 33.6 | 2.7 | 18 |
| 36 | 34.1 | 2.6 | 9 |
| 37 | 34.4 | 2.6 | 4 |
| 38 | 35.5 | 2.5 | 7 |
| 39 | 36.8 | 2.4 | 10 |
| 40 | 37.4 | 2.4 | 11 |

Further, the present invention is directed to a process for the preparation of crystalline (3R)-1-(2-methylalanyl-D-tryptophyl)-3-(phenylmethyl)-3-piperidinecarboxyl-ic acid 1,2,2-trimethylhydrazide which comprises crystallization of amorphous (3R)-1-(2-methylalanyl-D-tryptophyl)-3-(phenylmethyl)-3-piperid-inecarboxylic acid 1,2,2-trimethylhydrazide. In one embodiment, the method broadly includes crystallization of a solute from a solvent or slurry under conditions which yield crystalline (3R)-1-(2-methylalanyl-D-tryptophyl)-3-(phenylmethyl)-3-piperidinecarboxylic acid 1,2,2-trimethylhydrazide.

Thus, for example, crystalline (3R)-1-(2-methylalanyl-D-tryptophyl)-3-(phenylmethyl)-3-piperidinecarboxylic acid 1,2,2-trimethylhydrazide may be prepared by crystallization of the amorphous form, from a solution or from a slurry thereof in a solvent. In one embodiment, the solution or slurry of amorphous (3R)-1-(2-methylalanyl-D-tryptophyl)-3-(phenylmethyl)-3-piperidinecarboxylic acid 1,2,2-trimethylhydrazide in the solvent is formed by combining the (3R)-1-(2-methylalanyl-D-tryptophyl)-3-(phenylmethyl)-3-piperidinecar-boxylic acid 1,2,2-trimethylhydrazide with the solvent.

In another preferred embodiment, a solution of amorphous (3R)-1-(2-methylalanyl-D-tryptophyl)-3-(phenylmethyl)-3-piperidinecarboxylic acid 1,2,2-trimethylhydrazide in the solvent is formed by dissolving the (3R)-1-(2-methylalanyl-D-tryptophyl)-3-(phenylmethyl)-3-piperidinecar-boxylic acid 1,2,2-trimethylhydrazide in the solvent.

Suitable solvents are those from which (3R)-1-(2-methylalanyl-D-tryptophyl)-3-(phenylmethyl)-3-piperidinecarboxylic acid 1,2,2-trimethylhydrazide can be crystallized by the methods described herein. Examples of suitable solvents include those selected from the group consisting of alcohols (e.g., methanol, ethanol, n-propanol, isopropanol, butanol), polar organic solvents (e.g., dimethyl sulfoxide and ethylene glycol) and water.

In a preferred embodiment, the solvent is selected from the group comprising: methanol, ethanol, n-propanol, isopropanol, butanol, and mixtures thereof. In a more preferred embodiment, the solvent is methanol. In a most preferred embodiment, the solvent is a mixture of methanol and water containing, for example, between 5% and 95% v/v methanol, between 20% and 80% v/v methanol, preferably between 40% and 60% v/v methanol.

In another embodiment, crystalline (3R)-1-(2-methylalanyl-D-tryptophyl)-3-(phenylmethyl)-3-piperidinecarboxylic acid 1,2,2-trimethylhydrazide can be prepared from an aqueous-based solvent that includes, for example, between 5% and 95% v/v ethanol, between 20% and 80% v/v ethanol, and preferably between 40% and 60% v/v ethanol.

In a further embodiment, crystalline (3R)-1-(2-methylalanyl-D-tryptophyl)-3-(phenylmethyl)-3-piperidinecarboxylic acid 1,2,2-trimethylhydrazide can be prepared from an aqueous-based solvent that includes, for example, between 5% and 95% v/v isopropanol, between 20% and 80% v/v isopropanol, and preferably between 40% and 60% v/v isopropanol.

In one embodiment, the solvent may be heated to an elevated temperature. As used herein an "elevated temperature" is higher than ambient temperature, such as for example, between 40° C. and 100° C., between 50° C. and 80° C., or preferably between 65° C. and 75° C. In another embodiment, the solvent is heated to an elevated temperature prior to combining of (3R)-1-(2-methylalanyl-D-tryptophyl)-3-(phenylmethyl)-3-piperidinecarboxylic acid 1,2,2-trimethylhydrazide with the solvent. In another embodiment, the solvent is heated to an elevated temperature after combining (3R)-1-(2-methylalanyl-D-tryptophyl)-3-(phenylmethyl)-3-piperidinecarboxylic acid 1,2,2-trimethylhydrazide with the solvent.

In one embodiment, crystalline (3R)-1-(2-methylalanyl-D-tryptophyl)-3-(phenylmethyl)-3-piperidinecarboxylic acid 1,2,2-trimethylhydrazide is precipitated from the solvent. In one embodiment, precipitation is induced by concentration of the solution of (3R)-1-(2-methylalanyl-D-tryptophyl)-3-(phenylmethyl)-3-piperidinecarboxylic acid 1,2,2-trimethylhydrazide in the solvent by reduction of the volume of the solvent. The solvent may be reduced, for example, by evaporation of the solvent. In another embodiment, precipitation may be induced by allowing the solution of (3R)-1-(2-methylalanyl-D-tryptophyl)-3-(phenylmethyl)-3-piperidinecarboxylic acid 1,2,2-trimethylhydrazide in the solvent to cool.

In another embodiment, precipitation may be induced by rapidly cooling the solution, or by slowly cooling the solution. In a specific embodiment, precipitation may be induced by slowly cooling the solution to about 20° C. at a rate ranging from about 0.2° C./hr to about 20° C./hr, preferably from about 1° C./hr to about 10° C./hr. In a preferred embodiment, the solution is cooled from the initial elevated temperature to 60° C. at a rate of 20° C./h, then from 60° C. at a rate of 5° C./h, and then from 45° C. to ambient temperature at a rate of 15° C./h. The temperature and the cooling rate can be appropriately decided depending on the choice of solvent and the volume thereof. For the purpose of this invention ambient temperature is from about 20° C. to about 25° C.

In one embodiment, the precipitated crystalline (3R)-1-(2-methylalanyl-D-tryptophyl)-3-(phenylmethyl)-3-piperidinecarboxylic acid 1,2,2-trimethylhydrazide is isolated from the solvent. As used herein the term "isolated" encompasses crystalline (3R)-1-(2-methylalanyl-D-tryptophyl)-3-(phenylmethyl)-3-piperidinecarboxylic acid 1,2,2-trimethylhydrazide which is separated away from other material, such as the materials contained in the medium in which it was produced. In one embodiment, the isolated crystals are essentially free of chemicals or contaminating solvents from the source from which the crystals were derived or produced. In one embodiment, the crystals are isolated from the solvent by filtration of the solvent. In a preferred embodiment, the crystalline form is isolated from the solvent by filtration of the solvent after precipitation of the crystals.

In one embodiment, the isolated crystals are washed with, for example, a methanol/water mixture and dried in an oven. The crystals are preferably dried in an oven, at a temperature of between about ambient temperature and about 70° C., preferably from about 40° C. to about 60° C. Preferably, the drying takes place under vacuum.

In a further embodiment, "seeds" of the desired polymorph are added to the solvent in order to promote formation of a particular polymorph in the solvent. In one embodiment, the amorphous (3R)-1-(2-methylalanyl-D-tryptophyl)-3-(phenylmethyl)-3-piperidinecarboxylic acid 1,2,2-trimethylhydrazide is added to the solvent, and after cooling has begun the solvent is seeded with crystals of the desired polymorph. Alternatively, the seed crystals can be added once the solvent is saturated with amorphous of (3R)-1-(2-methylalanyl-D-tryptophyl)-3-(phenylmethyl)-3-piperidinecarboxylic acid 1,2,2-trimethylhydrazide.

In one embodiment the crystalline (3R)-1-(2-methylalanyl-D-tryptophyl)-3-(phenylmethyl)-3-piperidinecarboxylic acid 1,2,2-trimethylhydrazide is formed from 1-[(1R)-2-](3R)-3-Benzyl-3-(N,N',N'-trimethylhydrazinocarbonyl)piperidin-1-yl-]-1-(1H-indol-3-ylmethyl)-2-oxo-ethylcarbamoyl]-1-methylethyl carbamic acid ten-butyl ester. The tert-butoxycarbonyl group on 1-[(1R)-2-](3R)-3-Benzyl-3-(N,N',N'-trimethylhydrazinocarbonyl)piperidin-1-yl-]-1-(1H-indol-3-ylmethyl)-2-oxo-ethylcarbamoyl]-1-methylethyl}carbamic acid tert-butyl ester is removed to form the free amine in the presence of an acid. In one embodiment the acid is trifluoroacetic acid, hydrofluoric acid, hydrochloric acid, hydrobromic acid or sulfuric acid. In a preferred embodiment the acid is methanesulfonic acid. Once the tert-butoxycarbonyl group is removed, the mixture is neutralized using a base such as, for example, potassium hydroxide, sodium hydroxide, calcium hydroxide, ammonium hydroxide or potassium carbonate. In a preferred embodiment, the mixture is neutralized with a mixture of water and a base such as, for example, potassium hydroxide, sodium hydroxide, calcium hydroxide, ammonium hydroxide or potassium carbonate. The remainder of the crystallization process is carried out as described above.

In one embodiment, the present invention is crystalline (3R)-1-(2-methylalanyl-D-tryptophyl)-3-(phenylmethyl)-3-piperidinecarboxylic acid 1,2,2-trimethylhydrazide produced by the method described above. Variations in the methods of crystallization may produce variations in the crystals, including, for example, variations in the particle size and crystal density, which may result in variations in the XRPD patterns between crystal forms such as, for example, peak splitting, crystals produced by such methods are also encompassed by the present invention In one embodiment, form C of (3R)-1-(2-methylalanyl-D-tryptophyl)-3-(phenylmethyl)-3-piperidinecarboxylic acid 1,2,2-trimethylhydrazide can be produced by the methods described in Example 4 or Example 6, wherein a different XRPD spectrum is generated than by crystallization of form C (3R)-1-(2-methylalanyl-D-tryptophyl)-3-(phenylmethyl)-3-piperidinecarboxylic acid 1,2,2-trimethylhydrazide by slow evaporation from a solution thereof as described in Example 3.

"Slow evaporation" as used herein, means evaporation under atmospheric conditions or under an inert atmosphere of a solvent or mixture of solvents from a solution or slurry thereof with the compound to be crystallized.

In one embodiment, the present invention is a crystalline form C of (3R)-1-(2-methylalanyl-D-tryptophyl)-3-(phenylmethyl)-3-piperidinecarboxylic acid 1,2,2-trimethylhydrazide produced by the methods described in Example 4.

Figure 4:
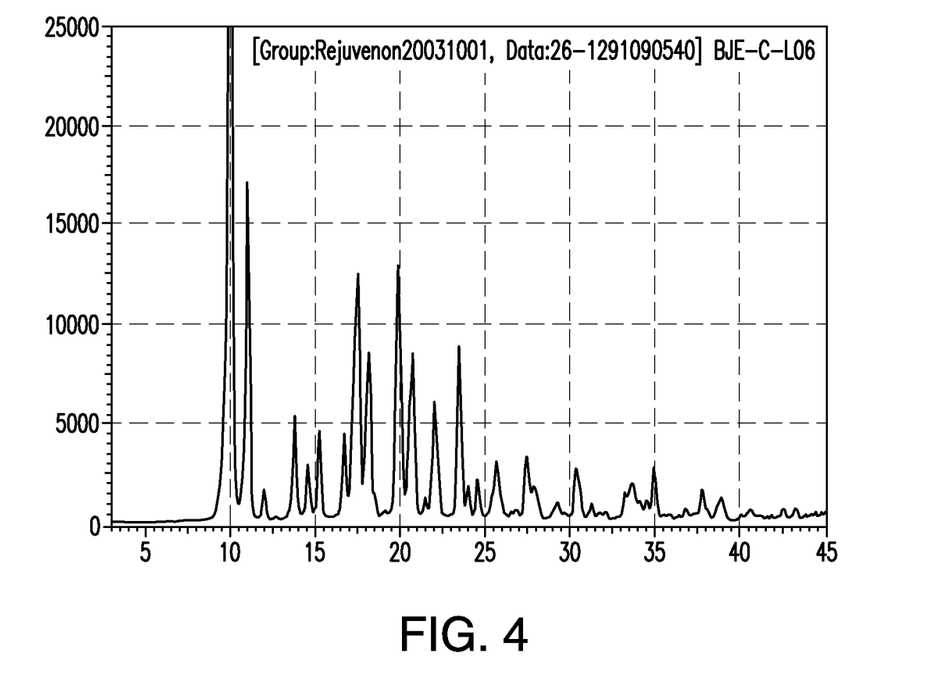
FIG. 4 is a characteristic X-Ray Powder Diffraction (XRPD) pattern for form C (3R)-1-(2-methylalanyl-D-tryptophyl)-3-(phenylmethyl)-3-piperidinecarboxylic acid 1,2,2-trimethylhydrazide produced by the method described in Example 8 (Vertical axis: Intensity (CPS); Horizontal axis: Diffraction Angle, in Two Theta (degrees).

In one embodiment, the present invention is a crystalline form C of (3R)-1-(2-methylalanyl-D-tryptophyl)-3-(phenylmethyl)-3-piperidinecarboxylic acid 1,2,2-trimethylhydrazide produced by the methods described in Example 6. In one embodiment crystalline form C of (3R)-1-(2-methylalanyl-D-tryptophyl)-3-(phenylmethyl)-3-piperidinecarboxylic acid 1,2,2-trimethylhydrazide is a monohydrate. In a preferred embodiment, crystalline form C of (3R)-1-(2-methylalanyl-D-tryptophyl)-3-(phenylmethyl)-3-piperidinecarboxylic acid 1,2,2-trimethylhydrazide is a dihydrate In another embodiment, the present invention is directed to crystalline form C dihydrate of (3R)-1-(2-methylalanyl-D-tryptophyl)-3-(phenylmethyl)-3-piperidinecarboxylic acid 1,2,2-trimethylhydrazide produced by the methods described in Example 8 characterized by the following X-ray powder diffraction pattern (also presented in FIG. 4) measured on a Shimadzu XRD-6000 X-ray powder diffractometer using Cu $K_\alpha$ radiation. Samples are placed on Si zero-return micro samples holders. The tube voltage and amperage are set to 40 kV and 40 mA, respectively. The divergence and scattering slits are set at 1° and the receiving slit is set at 0.30 mm. A theta-two theta continuous scan at 2°/min from 3.0 to 45° 2θ, with a sampling pitch of 0.02 deg and a preset time of 0.60 seconds. The X-ray powder diffraction pattern is expressed in terms of 2θ, d-spacings and relative intensities:

TABLE 4

Peak Data List for crystalline form C of (3R)-1-(2-methylalanyl-D-tryptophyl)-3-(phenylmethyl)-3-piperidinecarboxylic acid 1,2,3-trimethylhydrazide dihydrate.

| Peak No. | 2Theta (deg) | d (A) | Relative Intensity |
|---|---|---|---|
| 1 | 9.6 | 9.2 | 8 |
| 2 | 10.1 | 8.8 | 100 |
| 3 | 10.8 | 8.2 | 4 |
| 4 | 11.1 | 8.0 | 25 |
| 5 | 13.8 | 6.4 | 7 |
| 6 | 14.6 | 6.1 | 4 |
| 7 | 15.2 | 5.8 | 6 |
| 8 | 16.7 | 5.3 | 6 |
| 9 | 17.3 | 5.1 | 9 |
| 10 | 17.6 | 5.0 | 18 |
| 11 | 18.2 | 4.9 | 12 |
| 12 | 20.0 | 4.4 | 18 |
| 13 | 20.5 | 4.3 | 7 |
| 14 | 20.8 | 4.3 | 12 |
| 15 | 22.1 | 4.0 | 8 |
| 16 | 23.5 | 3.8 | 13 |
| 17 | 25.8 | 3.5 | 4 |
| 18 | 27.5 | 3.2 | 5 |
| 19 | 30.5 | 3.0 | 4 |
| 20 | 35.0 | 2.6 | 3 |

In another embodiment, crystalline form C dihydrate may be characterized by Differential Scanning Calorimetry (DSC) or by any other method known to persons skilled in the art.

In one embodiment, the present invention is directed to form C (3R)-1-(2-methylalanyl-D-tryptophyl)-3-(phenylmethyl)-3-piperidinecarboxylic acid 1,2,2-trimethylhydrazide dihydrate characterized by differential scanning calorimetry analysis (FIG. 5) which showed a broad endotherm centered at 68.5° C., followed by the melt endotherm with onset of 110° C. and peak of 116.8° C.

In another embodiment, the present invention is crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, at least four or at least five 2θ values measured using Cu $K_\alpha$ radiation are selected from the group consisting of about: 10.1, 11.1, 17.6, 20.0 and 20.8. In yet another embodiment, the present invention is a crystalline composition, having an X-ray powder diffraction pattern wherein at least one, at least two, at least three, at least four or at least five 2θ values measured using Cu $K_\alpha$ radiation are selected from the group listed above and at least one, at least two, at least three, at least four or at least five 2θ values measured using Cu $K_\alpha$ radiation are selected from the group consisting of about: 9.6, 17.3, 18.2, 22.1 and 23.5.

In another embodiment, the present invention is crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, at least four or at least five 2θ values measured using Cu $K_\alpha$ radiation are selected from the group consisting of about: 17.0, 19.4, 21.5, 26.2, and 33.3. In yet another embodiment, the present invention is a crystalline composition, having an X-ray powder diffraction pattern wherein at least one, at least two, at least three, at least four or at least five 2θ values measured using Cu $K_\alpha$ radiation are selected from the group listed above and at least one, at least two, at least three, at least four or at least five 2θ values measured using Cu $K_\alpha$ radiation are selected from the group consisting of about: 9.3, 23.3, 20.4, 22.9, and 23.5.

In another embodiment, the present invention is crystalline (3R)-1-(2-methylalanyl-D-tryptophyl)-3-(phenylmethyl)-3-piperidinecarboxylic acid 1,2,2-trimethylhydrazide having an X-ray, powder diffraction pattern wherein at least one, at least two, at least three, at least four or at least five 2θ values measured using Cu $K_\alpha$ radiation are selected from the group consisting of about: 19.2, 20.1, 23.0, 26.2, and 27.0. In yet another embodiment, the present invention is a crystalline composition, having an X-ray powder diffraction pattern wherein at least one, at least two, at least three, at least four or at least five 2θ values measured using Cu $K_\alpha$ radiation are selected from the group listed above and at least one, at least two, at least three, at least four or at least five 2θ values measured using Cu $K_\alpha$ radiation are selected from the group consisting of about: 16.3, 21.4, 24.0, 29.8, and 31.5.

In another embodiment, the present invention is crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, at least four or at least five 2θ values measured using Cu $K_\alpha$ radiation are selected from the group consisting of about 10.2, 11.2, 18.7, 20.6, and 23.4. In yet another embodiment, the present invention is a crystalline composition, having an X-ray powder diffraction pattern wherein at least one, at least two, at least three, at least four or at least five 2θ values measured using Cu $K_\alpha$ radiation are selected from the group listed above and at least one, at least two, at least three, at least four or at least five 2θ values measured using Cu $K_\alpha$ radiation are selected from the group consisting of about: 9.9, 13.8, 14.3, 16.7, and 19.8.

In another embodiment, the present invention is crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, or at least four 2θ values measured using Cu $K_\alpha$ radiation is selected from the group consisting of about: 10.1, 17.0, 20.6, and 23.0, and optionally at least two, at least three, or at least four additional 2θ values measured using Cu $K_\alpha$ radiation is selected from the group consisting: 17.6, 19.2, 23.0, 23.4, 26.2, and 33.3, or optionally at least two, at least three, at least four, at least five, at least six, at least seven, at least eight, or at least nine additional 2θ value measured using Cu $K_\alpha$ radiation is selected from the group consisting of about: 9.5, 16.7, 17.5, 17.9, 20.0, 21.5, 23.5, 23.9, and 27.5.

Further, the crystalline forms of (3R)-1-(2-methylalanyl-D-tryptophyl)-3-(phenylmethyl)-3-piperidinecarboxylic acid 1,2,2-trimethylhydrazide of the present invention are useful as pharmaceutical compositions.

In one embodiment, the present invention is a pharmaceutical composition comprising crystalline (3R)-1-(2-methylalanyl-D-tryptophyl)-3-(phenylmethyl)-3-piperidinecarboxylic acid 1,2,2-trimethylhydrazide as described herein and at least one pharmaceutically acceptable carrier or diluent.

Pharmaceutical compositions containing a polymorph of the present invention may be prepared by conventional techniques, as described in U.S. Pat. No. 6,576,648, the entire contents of which are incorporated herein by reference.

In another embodiment, the present invention relates to a pharmaceutical composition comprising, as an active ingredient, a polymorph of the present invention together with a pharmaceutically acceptable carrier or diluent.

The pharmaceutical carrier or diluent employed may be a conventional solid or liquid carrier. The carriers, diluents, preparation, composition, dosage and administration of the pharmaceutical compositions of the present invention are as described in U.S. Pat. No. 6,576,648, the entire contents of which are incorporated herein by reference.

The compound of the present invention is expected to possess the ability to release endogenous growth hormone in vivo. The compound may therefore be used in the treatment of conditions which require increased plasma growth hormone levels such as in growth hormone deficient humans or in elderly patients or livestock.

Thus, in one embodiment, the present invention is directed to a pharmaceutical composition for stimulating the release of growth hormone from the pituitary of a mammal, the composition comprising, as an active ingredient, a polymorph of the present invention together with a pharmaceutically acceptable carrier or diluent.

In one embodiment, the mammal, is a human, canine, murine, feline, bovine, ovine, swine or caprine. In a preferred embodiment, the mammal is a human.

Further the present invention is a method of stimulating the release of growth hormone from the pituitary of a mammal in need thereof, the method comprising administering to the mammal a therapeutically effective amount of a polymorph of the present invention.

As used herein, "a therapeutically effective amount" refers to an appropriate amount of active ingredient to obtain therapeutic or prophylactic effect and can be determined by standard pharmaceutical procedures in cell cultures or experimental animals.

In one embodiment, the present invention is a method of stimulating the release of growth hormone from the pituitary of a mammal, the method comprising administering to said mammal a therapeutically effective amount of crystalline (3R)-1-(2-methylalanyl-D-tryptophyl)-3-(phenylmethyl)-3-piperidinecarboxylic acid 1,2,2-trimethylhydrazide.

In another embodiment, the present invention is a method of stimulating the release of growth hormone from the pituitary of a mammal, the method comprising administering to said mammal a therapeutically effective amount of crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, at least four or at least five 2θ values measured using Cu $K_\alpha$ radiation are selected from the group consisting of about: 10.1, 11.1, 17.6, 20.0 and 20.8. In yet another embodiment, the present invention is a method of stimulating the release of growth hormone from the pituitary of a mammal, the method comprising administering to said mammal a therapeutically effective amount of crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, at least four or at least five 2θ values measured using Cu $K_\alpha$ radiation are selected from the group listed above and at least one, at least two, at least three, at least four or at least five 2θ values measured using Cu $K_\alpha$ radiation are selected from the group consisting of about: 9.6, 17.3, 18.2, 22.1 and 23.5.

In another embodiment, the present invention is a method of stimulating the release of growth hormone from the pituitary of a mammal, the method comprising administering to said mammal a therapeutically effective amount of crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, at least four or at least five 2θ values measured using Cu $K_\alpha$ radiation are selected from the group consisting of about: 17.0, 19.4, 21.5, 26.2, and 33.3. In yet another embodiment, the present invention is a method of stimulating the release of growth hormone from the pituitary of a mammal, the method comprising administering to said mammal a therapeutically effective amount of crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, at least four or at least five 2θ values measured using Cu K$_\alpha$ radiation are selected from the group listed above and at least two, at least three, at least four or at least five 2θ values measured using Cu K$_\alpha$ radiation are selected from the group consisting of about: 9.3, 23.3, 20.4, 22.9, and 23.5.

In another embodiment, the present invention is a method of stimulating the release of growth hormone from the pituitary of a mammal, the method comprising administering to said mammal a therapeutically effective amount of crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, at least four or at least five 2θ values measured using Cu K$_\alpha$ radiation are selected from the group consisting of about: 19.2, 20.1, 23.0, 26.2, and 27.0. In yet another embodiment, the present invention is a method of stimulating the release of growth hormone from the pituitary of a mammal, the method comprising administering to said mammal a therapeutically effective amount of crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, at least four or at least five 2θ values measured using Cu K$_\alpha$ radiation are selected from the group listed above and at least one, at least two, at least three, at least four or at least five 2θ values measured using Cu K$_\alpha$ radiation are selected from the group consisting of about: 16.3, 21.4, 24.0, 29.8, and 31.5.

In another embodiment, the present invention is a method of stimulating the release of growth hormone from the pituitary of a mammal, the method comprising administering to said mammal a therapeutically effective amount of crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, at least four or at least five 2θ values measured using Cu K$_\alpha$ radiation are selected from the group consisting of about 10.2, 11.2, 18.7, 20.6, and 23.4. In yet another embodiment, the present invention is a method of stimulating the release of growth hormone from the pituitary of a mammal, the method comprising administering to said mammal a therapeutically effective amount of crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, at least four or at least five 2θ values measured using Cu K$_\alpha$ radiation are selected from the group listed above and at least one, at least two, at least three, at least four or at least five 2θ values measured using Cu K$_\alpha$ radiation are selected from the group consisting of about: 9.9, 13.8, 14.3, 16.7, and 19.8.

In another embodiment, the present invention is a method of stimulating the release of growth hormone from the pituitary of a mammal, the method comprising administering to said mammal a therapeutically effective amount of crystalline (3R)-1-(2-methylalanyl-D-tryptophyl)-3-(phenylmethyl)-3-piperidinecarboxylic acid 1,2,2-trimethylhydrazide having an X-ray powder diffraction pattern wherein at least one, at least two, at least three, or at least four 2θ values measured using Cu K$_\alpha$ radiation is selected from the group consisting of about: 10.1, 17.0, 20.6, and 23.0, and optionally at least two, at least three, or at least four additional 2θ values measured using Cu K$_\alpha$ radiation is selected from the group consisting: 17.6, 19.2, 23.0, 23.4, 26.2, and 33.3, or optionally at least two, at least three, at least four, at least five, at least six, at least seven, at least eight, or at least nine additional 2θ value measured using Cu K$_\alpha$ radiation is selected from the group consisting of about: 9.5, 16.7, 17.5, 17.9, 20.0, 21.5, 23.5, 23.9, and 27.5.

To those skilled in the art, it is well known that the current and potential uses of growth hormone in humans are varied and multitudinous. Thus, the polymorph of the present invention can be administered for purposes stimulating release of growth hormone from the pituitary and would then have similar effects or uses as growth hormone itself. The polymorphs of the present invention are expected to be useful, for example, for stimulation of growth hormone release in the elderly, prevention of catabolic side effects of glucocorticoids, prevention and treatment of osteoporosis, treatment of chronic fatigue syndrome (CFS), treatment of acute fatigue syndrome and muscle loss following elective surgery, stimulation of the immune system, acceleration of wound healing, accelerating bone fracture repair, accelerating complicated fractures, e.g. distraction osteogenesis, treatment of wasting secondary to fractures, treatment of growth retardation, treating growth retardation resulting from renal failure or insufficiency, treatment of cardiomyopathy, treatment of wasting in connection with chronic liver disease, treatment of thrombocytopenia, treatment of growth retardation in connection with Crohn's disease, treatment of short bowel syndrome, treatment of wasting in connection with chronic obstructive pulmonary disease (COPD), treatment of complications associated with transplantation, treatment of physiological short stature including growth hormone deficient children and short stature associated with chronic illness, treatment of obesity and growth retardation associated with obesity, treatment of anorexia, treating growth retardation associated with the Prader-Willi syndrome and Turner's syndrome; increasing the growth rate of a patient having partial growth hormone insensitive syndrome, accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of catabolism in connection with pulmonary dysfunction and ventilator dependency; treatment of cardiac failure or related vascular dysfunction, treatment of impaired cardiac function, treatment or prevention of myocardial infarction, lowering blood pressure, protection against ventricular dysfunction or prevention of reperfusion events; treatment of adults in chronic dialysis; attenuation of protein catabolic responses after major surgery, reducing cachexia and protein loss due to chronic illness such as cancer or AIDS; treatment of hyperinsulinemia including nesidioblastosis, adjuvant treatment for ovulation induction; stimulation of thymic development and prevention of the age-related decline of thymic function, treatment of immunosuppressed patients; treatment of sarcopenia, treatment of wasting in connection with AIDS; improvement in muscle strength, mobility, maintenance of skin thickness, metabolic homeostasis and renal homeostasis in the frail elderly, stimulation of osteoblasts, bone remodelling and cartilage growth; regulation of food intake; stimulation of the immune system in companion animals and treatment of disorder of aging in companion animals, promoting growth in livestock and stimulation of wool growth in sheep, increasing milk production in livestock, treatment of metabolic syndrome (syndrome X), treatment of insulin resistance, including NIDDM, in mammals, e.g. humans, treatment of insulin resistance in the heart, improvement of sleep quality and correction of the relative hyposomatotropism of senescence due to high increase in REM sleep and a decrease in REM latency, treatment of hypothermia, treatment of frailty associated with ageing, treatment of congestive heart failure, treatment of hip fractures, treatment of immune deficiency in individuals with a depressed T4/T8 cell ratio, treatment of muscular atrophy, treatment of musculoskeletal impairment in elderly, enhancing the activity of protein kinase B (PKB), improvement of the overall pulmonary function, treatment of sleep disorders, treatment of growth retardation in connection with asthma, treatment of growth retardation in connection with juvenile rheumatic arthritis, and treatment of growth retardation in connection with cystic fibrosis.

Optionally, the pharmaceutical composition of the invention may comprise a polymorph of the present invention combined with one or more compounds exhibiting a different activity, e.g., an antibiotic or other pharmacologically active material.

Apart from the pharmaceutical use of a polymorph of the present invention, it may be useful in vitro tools for investigating the regulation of growth hormone release.

The polymorphs of the present invention may also be a useful in vivo tool for evaluating the growth hormone releasing capability of the pituitary. For example, serum samples taken before and after administration of the polymorph to humans can be assayed for growth hormone. Comparison of the growth hormone in each serum sample would directly determine the ability of the patient's pituitary to release growth hormone.

The polymorph of the present invention may be administered to commercially important animals to increase their rate and extent of growth, and to increase milk production.

A further use of the polymorph of the present invention is in combination with other secretagogues such as GHRP (2 or 6), GHRH and its analogues, growth hormone and its analogues or somatomedins including IGF-1 and IGF-2.

The invention will now be described more specifically by the examples.

Example 1

Figure 1:
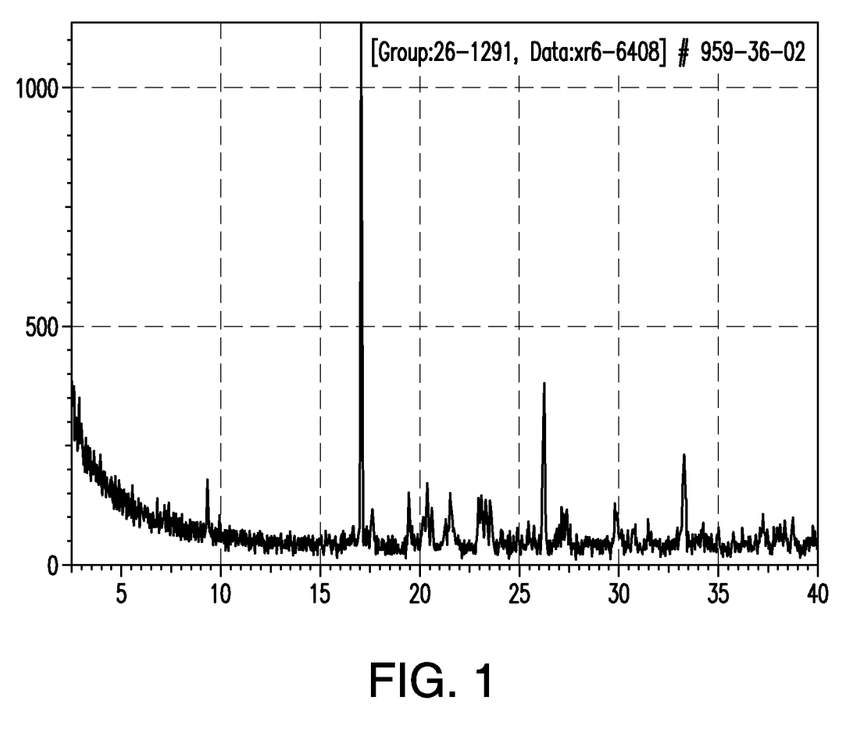
FIG. 1 is a characteristic X-Ray Powder Diffraction (XRPD) pattern for form A (3R)-1-(2-methylalanyl-D-tryptophyl)-3-(phenylmethyl)-3-piperidinecarboxylic acid 1,2,2-trimethylhydrazide produced by the method described in Example 1 (Vertical axis: Intensity (CPS); Horizontal axis: Diffraction Angle, in Two Theta (degrees).

Crystallization of (3R)-1-(2-methylalanyl-D-tryptophyl)-3-(phenylmethyl)-3-piperidinecarboxylic acid 1,2,2-trimethylhydrazide form A 0.0103 g of (3R)-1-(2-methylalanyl-D-tryptophyl)-3-(phenylmethyl)-3-piperidinecarboxylic acid 1,2,2-trimethylhydrazide was dissolved in methanol (0.1 mL) in a glass vial. The glass vial was then covered with PARAFILM® (thermoplastic film) which was perforated with a single hole. The solvent was then allowed to evaporate under ambient conditions. An X-ray diffraction pattern showed the compound was crystalline (FIG. 1).

Example 2

Figure 2:
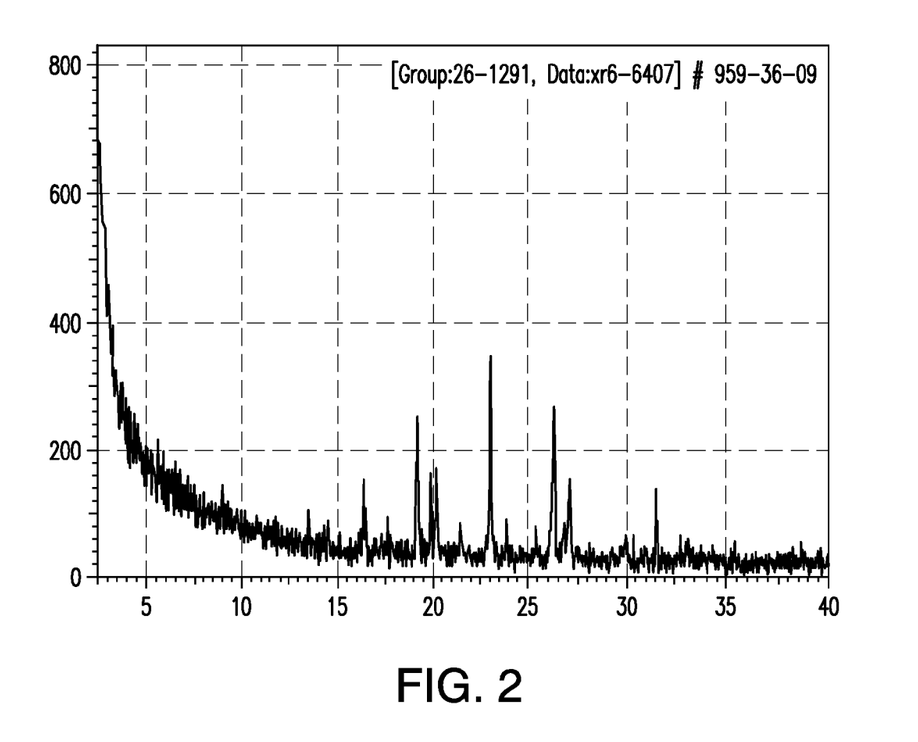
FIG. 2 is, a characteristic X-Ray Powder Diffraction (XRPD) pattern for form B (3R)-1-(2-methylalanyl-D-tryptophyl)-3-(phenylmethyl)-3-piperidinecarboxylic acid 1,2,2-trimethylhydrazide produced by the method described in Example 2 (Vertical axis: Intensity (CPS); Horizontal axis: Diffraction Angle, in Two Theta (degrees).

Crystallization of (3R)-1-(2-methylalanyl-D-tryptophyl)-3-(phenylmethyl)-3-piperidinecarboxylic acid 1,2,2-trimethylhydrazide form B 0.0124 g of (3R)-1-(2-methylalanyl-D-tryptophyl)-3-(phenylmethyl)-3-piperidinecarboxylic acid 1,2,2-trimethylhydrazide was dissolved in methanol:water (2:1) mixture (0.15 mL) in a glass vial. The glass vial was then covered with PARAFILM® (thermoplastic film) which was perforated with a single hole. The solvent was then allowed to evaporate under ambient conditions. An X-ray diffraction pattern showed the compound was crystalline (FIG. 2).

Example 3

Crystallization of (3R)-1-(2-methylalanyl-D-tryptophyl)-3-(phenylmethyl)-3-piperidinecarboxylic acid 1,2,2-trimethylhydrazide form C 0.1003 g of (3R)-1-(2-methylalanyl-D-tryptophyl)-3-(phenylmethyl)-3-piperidinecarboxylic acid 1,2,2-trimethylhydrazide was added to methanol (2 mL) in a glass vial. The mixture was filtered into a clean vial. The glass vial was then covered with PARAFILM® (thermoplastic film) which was perforated with a single hole. The solvent was then allowed to evaporate under ambient conditions. XRPD analysis of (3R)-1-(2-methylalanyl-D-tryptophyl)-3-(phenylmethyl)-3-piperidinecarboxylic acid 1,2,2-trimethylhydrazide indicated that the molecule was crystalline [data not shown].

Example 4

Crystallization of (3R)-1-(2-methylalanyl-D-tryptophyl)-3-(phenylmethyl)-3-piperidinecarboxylic acid 1,2,2-trimethylhydrazide form C {1-[(1R)-2-](3R)-3-Benzyl-3-(N,N',N'-trimethylhydrazinocarbonyl)piperidin-1-yl-]-1-(1H-indol-3-ylmethyl)-2-oxo-ethylcarbamoyl]-1-methylethyl}-carbamic acid tert-butyl ester (4.72 kg) was dissolved in methanol (5 L/kg) and heated to 55+/−5° C. Methanesulfonic acid (1.5 equiv) was added dropwise over 45 minutes while maintaining a temperature of 55+/−5. ° C. After the addition was complete, the batch temperature was increased and maintained at 60+/−5° C. The progress of the reaction was monitored using HPLC Upon the completion of the deprotection, the batch was heated to 70+/−5° C. and a solution of potassium hydroxide (3 equiv) in water (5 L/kg of Boc-protected compound) was added dropwise over 2 hours while maintaining the temperature. The heat was then removed from the vessel and the batch was allowed to cool to 22° C. over 41 hours. The batch was filtered and the cake was washed with 50% aqueous methanol followed by water. The filter cake was then slurried in water at 50+/−5° C. for 24 hours, filtered, and washed with water. The filter cake was again slurried in water at 50+/5° C. for 17 hours, filtered, and washed with water. The product was then loaded onto trays and dried under vacuum at 70+/−5° C. The final yield of crystalline (3R)-1-(2-methylalanyl-D-tryptophyl)-3-(phenylmethyl)-3-piperidinecarboxylic acid 1,2,2-trimethylhydrazide was 3.25 kg (81%) with a purity of 99.8 area % by HPLC Moisture of this product was determined using Karl Fischer in two separate measurements to be 2.4% and 3.2%, which indicates that the sample is in a monohydrate form In an alternative embodiment the steps of slurring the filter cake in purified water at 50+/−5° C. for 24 hours, refiltering, and washing with purified water, and repeating the slurry/filter/wash process can be omitted.

Example 5

Figure 3:
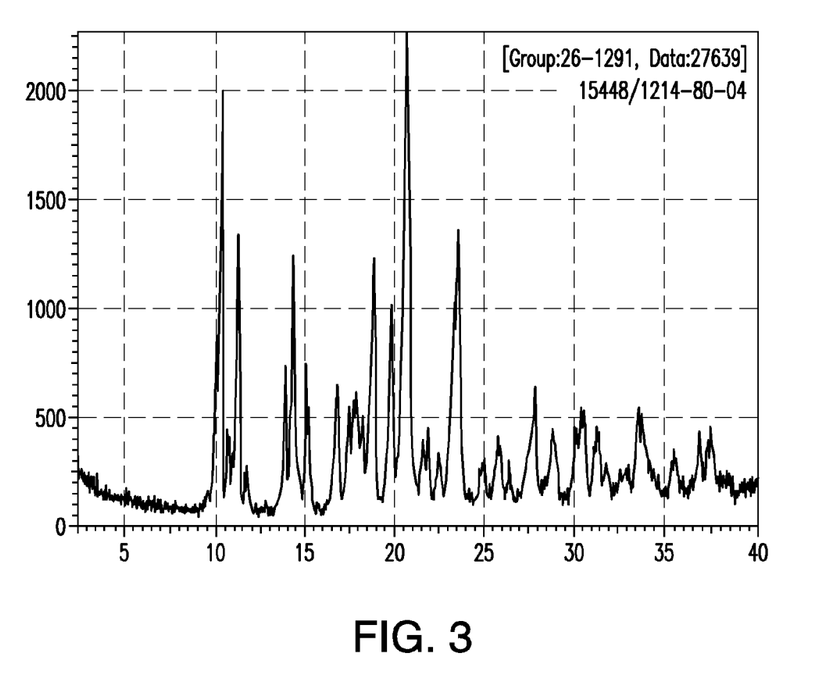
FIG. 3 is a characteristic X-Ray Powder Diffraction (XRPD) pattern for form D (3R)-1-(2-methylalanyl-D-tryptophyl)-3-(phenylmethyl)-3-piperidinecarboxylic acid 1,2,2-trimethylhydrazide produced by the method described in Example 5 (Vertical axis: Intensity (CPS); Horizontal axis: Diffraction Angle, in Two Theta (degrees).

Preparation of (3R)-1-(2-methylalanyl-D-tryptophyl)-3-(phenylmethyl)-3-piperidinecarboxylic acid 1,2,2-trimethylhydrazide form D 15 g of crystalline (3R)-1-(2-methylalanyl-D-tryptophyl)-3-(phenylmethyl)-3-piperidinecarboxylic acid 1,2,2-trimethylhydrazide was produced by the method described in Example 4 except that the steps in which the filter cake was reslurried in water at 50+/−5° C. were omitted and the product was dried at room temperature in a vacuum oven. This sample was charged to a vessel with 76 mL (5 vol) water. The mixture was heated to 50° C. under moderate stirring overnight (16 h). The still warm mixture was filtered through Whatman #1 filter paper, washed with water (15 mL; 1 vol) and dried in a vacuum oven at 60° C. for 54 hours and then dried at 70. ° C. for 120 hours. An X-ray diffraction pattern showed the compound was crystalline (FIG. 3).

Example 6

Crystallization of (3R)-1-(2-methylalanyl-D-tryptophyl)-3

(3R)-1-(2-methylalanyl-D-tryptophyl)-3-(phenylmethyl)-3-piperidinecarboxylic acid 1,2,2-trimethylhydrazide amorphous was suspended in methanol (5 L/kg) and the mixture was heated to 65° C. while being stirred. Water (4 L/kg) was then added slowly while the temperature was maintained between 65-68° C. After the addition was complete the mixture was cooled to 60° C. at a rate of 20° C./h, then from 60° C. to 45° C. at a rate of 5° C./h, and then from 45° C. to ambient temperature at a rate of 15° C./h. The crystals were filtered and washed with methanol-water (5:4 1.5 L/kg) and dried in vacuo.

Using this protocol approximately 175 g of (3R)-1-(2-methylalanyl-D-tryptophyl)-3-(phenylmethyl)-3-piperidinecarboxylic acid 1,2,2-trimethylhydrazide with a purity of 99.3% area was isolated under traceable conditions from crude (3R)-1-(2-methylalanyl-D-tryptophyl)-3-(phenylmethyl)-3-piperidinecarboxylic acid 1,2,2-trimethylhydrazide (approximately 90 area %).

XRPD analysis of (3R)-1-(2-methylalanyl-D-tryptophyl)-3-(phenylmethyl)-3-piperidinecarboxylic acid 1,2,2-trimethylhydrazide indicated that the molecule was crystalline [data not shown]. KF analysis showed that the sample contained 2.1% water. OVI results showed that the product contained methanol of 1.9%.

Example 7

Hygroscopicity Study of (3R)-1-(2-methylalanyl-D-tryptophyl)-3-(phenylmethyl)-3-piperidinecarboxylic acid 1,2,2-trimethylhydrazide (form C)

The hygroscopicity of (3R)-1-(2-methylalanyl-D-tryptophyl)-3-(phenylmethyl)-3-piperidinecarboxylic acid 1,2,2-trimethylhydrazide form C produced by the method disclosed in Example 4 (monohydrate) was evaluated using Dynamic Vapor Sorption analysis (DVS) and Thermogravimetric analysis (TGA).
Dynamic Vapor Sorption Analysis (DVS)
The samples were analyzed using a Hiden IGAsorp vapor sorption analyzer. Each sample was placed in a sample pan and exposed to drying at 25° C. in a dry nitrogen stream for two hours. This assured that the samples being analyzed were at a constant weight prior to the start of the analysis. The samples were then analyzed at 25.0° C. The adsorption isotherm was conducted between: 10-90% RH with a step size of 10%. The desorption isotherm was conducted between 85-0% RH with a step size 10%. After the isotherms were complete, each of the samples were heated to 125° C. until the weight loss curve reached an asymptote or for 4 hours.
Thermogravimetric Analysis (TGA)
The samples were analyzed using a Mettler 851e thermogravimetric analyzer. Samples were weighed into a crucible. The samples were heated from 30° C. to 300.0° C. ramped at 10.00° C./min with an air purge.

The (3R)-1-(2-methylalanyl-D-tryptophyl)-3-(phenylmethyl)-3-piperid-inecarboxylic acid 1,2,2-trimethylhydrazide initially contained 2.5% by weight bound water (shown by TGA analysis). Bound water was identified by a step transition in the TGA thermogram. DVS analysis showed that during the adsorption isotherm the sample adsorbed water steadily until it contained 6% by weight at 35% RH which indicated the presence of a stable dihydrate. No other significant additional adsorption was observed up to 90% RH. During the desorption isotherm, the dihydrate form was observed down to 30% RH after which desorption of moisture occurred.

In conclusion DVS results showed that the dihydrate was formed above a relative humidity of 35%.

Example 8

Preparation of (3R)-1-(2-methylalanyl-D-tryptophyl)-3-(phenylmethyl)-3-piperidinecarboxylic acid 1,2,2-trimethylhydrazide form C dihydrate and characterization of (3R)-1-(2-methylalanyl-D-tryptophyl)-3-(phenylmethyl)-3-piperidinecarboxylic acid 1,2,2-trimethylhydrazide form C monohydrate and (3R)-1-(2-methylalanyl-D-tryptophyl)-3-(phenylmethyl)-3-piperidinecarboxylic acid 1,2,2-trimethylhydrazide form C dihydrate One gram of crystalline (3R)-1-(2-methylalanyl-D-tryptophyl)-3-(phenylmethyl)-3-piperidinecarboxylic acid 1,2,2-trimethylhydrazide produced by the method of Example 4 (monohydrate) was spread evenly on a Petri dish and equilibrated in a desiccator over a saturated solution of $BaCl_2 2H_2O$ for 2.5 days. The relative humidity in this environment was ~90%. The conversion to the dihydrate was confirmed by sample weight measurement before and after equilibration.

The starting material (monohydrate) and dihydrate were then analyzed by DSC, and KF. XRPD was performed which investigated if moisture sorption altered the crystal lattice of the starting material.
X-Ray Powder Diffraction (XRPD)
The X-ray powder diffraction patterns were measured on a Shimadzu XRD-6000 X-ray powder diffractometer using Cu $K_\alpha$ radiation. Samples were placed on Si zero-return micro samples holders. The tube voltage and amperage were set to 40 kV and 40 mA, respectively. The divergence and scattering slits were set at 1° and the receiving slit was set at 0.30 mm. A theta-two theta continuous scan at 2°/min from 3.0 to 45° 2θ, with a sampling pitch of 0.02 deg and a preset time of 0.60 seconds.
Differential Scanning Calorimetry Analysis (DSC)
Samples were analyzed using a Mettler 821e Differential Scanning Calorimeter DSC Samples were weighed in pan, covered with a pierced lid and then crimped (sealed). Analysis conditions were 30-300.0° C. ramped at 10° C./min with a nitrogen purge.

XRPD analysis of (3R)-1-(2-methylalanyl-D-tryptophyl)-3-(phenylmethyl)-3-piperidinecarboxylic acid 1,2,2-trimethylhydrazide monohydrate indicated that the molecule was crystalline. DSC analysis showed an endothermic transition with onset of 109.5° C. and peak value of 116.4° C. The extended onset was believed to be due to dehydration of the material. KF analysis showed that the sample contained 2.4% water. This corresponded to an average molar ratio of water/sample of 0.8 or =~1, which would indicate the compound was a monohydrate.

Figure 5:
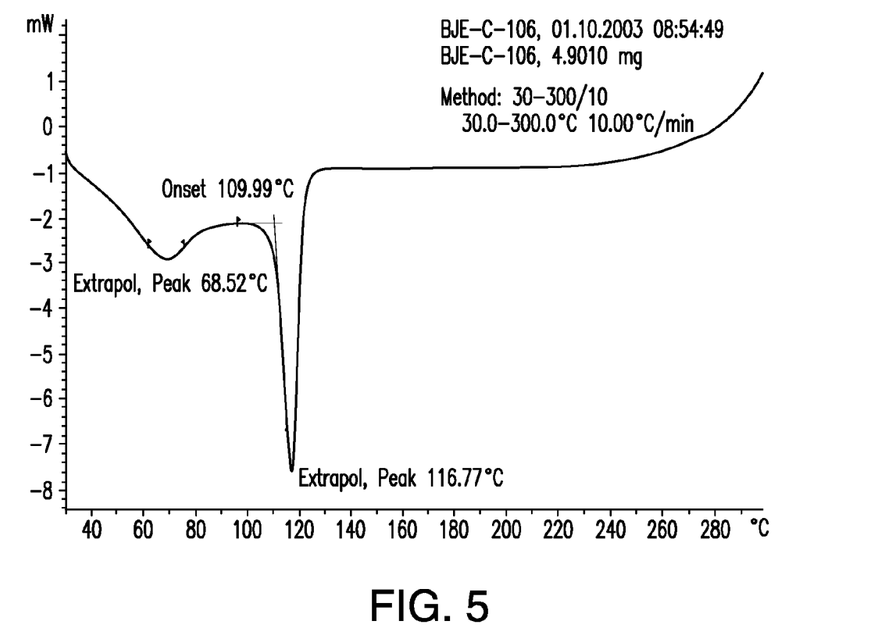
FIG. 5 is a characteristic Differential Scanning Calorimetry (DSC) thermogram for form C (3R)-1-(2-methylalanyl-D-tryptophyl)-3-(phenylmethyl)-3-piperidinecarboxylic acid 1,2,2-trimethylhydrazide as described in Example 8.

XRPD results of (3R)-1-(2-methylalanyl-D-tryptophyl)-3-(phenylmethyl)-3-piperidinecarboxylic acid 1,2,2-trimethylhydrazide dihydrate indicated that the molecule was crystalline (FIG. 4) and exhibited a similar pattern to the monohydrate starting material. DSC analysis showed a broad endotherm centered at 68.5° C. due to water loss followed by the melt endotherm with onset of 110° C. and peak of 116.8° C. (FIG. 5). KF analysis showed that the sample contained 5.6% water. This corresponded to an average molar ratio of water/sample of 1.7 or ~2.0, which would indicate the compound was a dihydrate.

XRPD results indicated that both the monohydrate and its dihydrate were crystalline and exhibited similar powder patterns. DSC and KF results confirmed the formation of the dihydrate from the monohydrate.

Example 9

Stability of crystalline (3R)-1-(2-methylalanyl-D-tryptophyl)-3-(phenylmethyl)-3-piperidinecarboxylic acid 1,2,2-trimethylhydrazide Crystalline (3R)-1-(2-methylalanyl-D-tryptophyl)-3-(phenylmethyl)-3-piperidinecarboxylic acid 1,2,2-trimethylhydrazide was placed in double plastic bags, closed under a nitrogen blanket, and placed inside a small fiberboard container, the physical appearance, water content, purity and crystallinity were tested every three months for a period of 12 months under a variety of conditions. The results of this study can be seen in Table 5.

The purity and water content of (3R)-1-(2-methylalanyl-D-tryptophyl)-3-(phenylmethyl)-3-piperidinecarboxylic acid 1,2,2-trimethylhydrazide was analyzed using HPLC and KF respectively before, during, and after the 12 month stability study. As can be seen from Table 5 the purity of crystalline (3R)-1-(2-methylalanyl-D-tryptophyl)-3-(phenylmethyl)-3-piperidinecarboxylic acid 1,2,2-trimethylhydrazide was relatively unchanged after 12 months. Karl Fischer Analysis found that the water content increased from 3.2% to approximately 6% after 12 months.

TABLE 5

12 month stability study

| Test (Test Minded) | Specifications | Storage Conditions | Initial | 1 | 3 | 6 | 9 | 12 | 18 | 24 | 36 |
|---|---|---|---|---|---|---|---|---|---|---|---|
| Physical Description (TM-106) | White to off-white solid | 5° C. | Off-white solid | Off-white solid | Off-white solid | Off-white solid | White solid | Off-white solid | | | |
| | | 25° C. 60% RH | | Off-white solid | Off-white solid | Off-white solid | Off-white solid | Off-white solid | | | |
| | | 30° C. 60% RH | | — | — | — | — | — | | | |
| | | 40° C. 60% RH | | Off-white solid | Off-white solid | Off-white solid | — | — | | | |
| Water content by Karl Fisher (USP <921> method 1 of SOP INS002) | For Information Only | 5° C. | 3_% | 5.3% | 6.0% | 5.8% | 5.6% | 6.1% | | | |
| | | 25° C. 60% RH | | 5.8% | 6.0% | 5.9% | 5.7% | 5.8% | | | |
| | | 30° C. 60% RH | | — | — | — | — | — | | | |
| | | 40° C. 75% RH | | 6.1% | 6.1% | 5.9% | — | — | | | |
| HPLC Weight % (TM-808) | For Information Only | 5° C. | 99.8% | 92.0% | 93.2% | 93.9% | 94.5% | 94.3% | | | |
| | | 25° C. 60% RH | | 92.1% | 93.2% | 94.2% | 94.6% | 94.2% | | | |
| | | 30° C. 60% RH | | — | — | — | — | — | | | |
| | | 40° C. 75% RH | | 91.8% | 93.0% | 94.1% | — | — | | | |
| HPLC Area % (TM-808)[1] | Not Less Than 95% | 5° C. | 99.8% | 99.7% | 99.7% | 99.7 | 99.8% | 99.7% | | | |
| | | 25° C. 60% RH | | 99.7% | 99.7% | 99.7 | 99.8% | 99.7% | | | |
| | | 30° C. 60% RH | | — | — | — | — | — | | | |
| | | 40° C. 75% RH | | 99.7% | 99.7% | 99.7 | — | — | | | |
| DSC (USP <891>, SUP INS034) | For Information Only | 5° C. | Onset 108.2° C. Peak: 112.7° C. | Onset: 81.8° C. Peak: 110.4° C. Onset: 116.0° C. Peak: 118.4° C. | Onset: 112.1° C. Peak: 117.1° C. | Onset: 112.3° C. Peak: 116.9° C. | — | — | | | |
| | | 25° C. 60% RH | | Onset: 107.0° C. Peak: 110.3° C. Onset: 121.3° C. Peak: 122.2° C. | Onset: 112.6° C. Peak: 117.7° C. | Onset: 112.5° C. Peak: 116.9% | | | | | |
| | | 30° C. 60% RH | | — | | | | | | | |
| | | 40° C. 75% RH | | Onset: 89.2° C. Peak: 110.3° C. Onset: 129.9° C. Peak: 134.9° C. Onset: 151.1° C. Peak: 165.2° C. | Onset: 112.2° C. Peak: 117.5° C. | Onset: 125.5° C. Peak: 117.8° C. | — | — | | | |

TABLE 5-continued 12 month stability study

| Test (Test Minded) | Specifications | Storage Conditions | Interval (Months) | | | | | | | | |
|---|---|---|---|---|---|---|---|---|---|---|---|
| | | | Initial | 1 | 3 | 6 | 9 | 12 | 18 | 24 | 36 |
| Crystallinity using Optical Microscopy (USP<695>) | For Information only | 5° C. | Crystallize | Crystallize | Crystallize | Crystallize | Crystallize | Crystallize | | | |
| | | 25° C. 60% RH | | Crystallize | Crystallize | Crystallize | Crystallize | Crystallize | | | |
| | | 30° C. 60% RH | | — | — | — | — | — | | | |
| | | 40° C. 75% RH | Crystallize | Crystallize | Crystallize | — | — | | | | |

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. Crystalline (3R)-1-(2-methylalanyl-D-tryptophyl)-3-(phenylmethyl)-3-piperidinecarboxylic acid 1,2,2-trimethylhydrazide (anamorelin) monohydrate having an X-ray powder diffraction pattern having at least four 2θ values measured using Cu Kα radiation selected from the group consisting of 10.1, 11.1, 17.6, 20.0, and 20.8.

2. The crystalline anamorelin monohydrate of claim 1, comprising methanol as an organic volatile impurity.

3. A process for preparing the crystalline anamorelin monohydrate of claim 1 comprising: a) producing a mixture of anamorelin and a solvent comprised of methanol and water; b) precipitating crystalline anamorelin from the solvent; and c) isolating the crystalline anamorelin.

4. The process of claim 3, wherein the solvent is a mixture of water and methanol and the volume percentage of methanol in the mixture is from about 5% to about 95%.

5. The process of claim 3, wherein the solvent is a mixture of water and methanol and the volume percentage of methanol in the mixture is from about 20% to about 80%.

6. The process of claim 3, wherein the solvent is a mixture of water and methanol and the volume percentage of methanol in the mixture is from about 40% to about 60%.

7. The process of claim 3, wherein the solvent is at an elevated temperature while combining with the anamorelin in step a), or the solvent is heated to an elevated temperature after combining with the anamorelin in step a).

8. The process of claim 7, wherein said elevated temperature is from about 40° C. to about 100° C.

9. The process of claim 7, wherein said elevated temperature is from about 50° C. to about 80° C.

10. The process of claim 7, wherein said elevated temperature is from about 65° C. to about 75° C.

11. The process of claim 3, wherein the crystals are precipitated in step b) by cooling the solvent.

12. A process for preparing the crystalline anamorelin monohydrate of claim 1 comprising: a) combining {1-[(1R)-2-](3R)-3-Benzyl-3-(N,N,N'-trimethylhydrazinocarbonyl)piperidin-1-yl-]-1-(1H-indol-3-ylmethyl)-2-oxo-ethylcarbamoyl]-1-methylethyl}carbamic acid tert-butyl ester (protected anamorelin) with a solvent; b) combining the mixture from step a) with an acid; c) neutralizing the mixture formed in step b); d) precipitating crystals of anamorelin from the solvent; and e) isolating the crystals.

13. The process of claim 12, wherein the solvent in step a) is methanol, and the mixture is neutralized in step c) with a mixture of potassium hydroxide and water.

14. The process of claim 12, wherein the acid is methanesulfonic acid.

15. The process of claim 12, wherein the solvent is at an elevated temperature while combining with said protected anamorelin in step a), or the solvent is heated to an elevated temperature after combining with said protected anamorelin in step a).

16. The process of claim 15, wherein the elevated temperature is from about 50° C. to about 75° C.

17. The process of claim 12, wherein the crystals are precipitated in step d) by cooling the solvent.

* * * * *